United States Patent
Castro et al.

(10) Patent No.: US 10,478,184 B2
(45) Date of Patent: Nov. 19, 2019

(54) SYSTEM FOR CONTROLLING A TISSUE-STAPLING OPERATION

(71) Applicant: Boston Scientific Scimed, Inc., Maple Grove, MN (US)

(72) Inventors: Carlos Castro, San Jose, CA (US); Amador Hallare, Newark, CA (US); Hollie Pope, Menlo Park, CA (US); David Cole, Weybridge, VT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 320 days.

(21) Appl. No.: 15/410,333

(22) Filed: Jan. 19, 2017

(65) Prior Publication Data

US 2017/0189025 A1   Jul. 6, 2017

Related U.S. Application Data

(63) Continuation of application No. 14/203,951, filed on Mar. 11, 2014, now Pat. No. 9,579,100.
(Continued)

(51) Int. Cl.
*A61B 17/072* (2006.01)
*A61B 17/068* (2006.01)
(Continued)

(52) U.S. Cl.
CPC .. *A61B 17/07207* (2013.01); *A61B 17/00234* (2013.01); *A61B 17/068* (2013.01);
(Continued)

(58) Field of Classification Search
CPC .............. A61B 17/068; A61B 17/072; A61B 17/07207; A61B 17/115; A61B 17/1155;
(Continued)

(56) References Cited

U.S. PATENT DOCUMENTS 5,632,432 A * 5/1997 Schulze ........... A61B 17/07207
227/176.1
5,897,562 A * 4/1999 Bolanos ........... A61B 17/07207
227/176.1
(Continued)

FOREIGN PATENT DOCUMENTS

EP   1 736 104 A1   12/2006
JP   2003/019138 A   1/2003
(Continued)

OTHER PUBLICATIONS

International Search Report dated Aug. 8, 2014 in International Appln. No. PCT/US2014/023123 filed Mar. 11, 2014.
(Continued)

*Primary Examiner* — Scott A Smith
(74) *Attorney, Agent, or Firm* — Bookoff McAndrews, PLLC

(57) ABSTRACT

An endoscopic stapler is disclosed. The stapler includes a staple member and an anvil member. The staple member may include a staple housing and the staple holder may include one or more staples. The anvil member may be spaced apart from the staple member and may configured to relatively move towards one another. A controller may be fluidly coupled to the staple member through a plurality of conduits. The controller may be configured to (a) direct a pressurized fluid to the staple member through a first conduit of the plurality of conduits to relatively move the staple member and the anvil member towards one another, and (b) direct the pressurize fluid through a second conduit of the plurality of conduits to eject one or more staples from the staple holder.

18 Claims, 8 Drawing Sheets

Related U.S. Application Data

(60) Provisional application No. 61/801,344, filed on Mar. 15, 2013.

(51) Int. Cl.

| | | |
|---|---|---|
| *A61B 17/00* | (2006.01) | |
| *A61B 17/115* | (2006.01) | |
| A61B 17/30 | (2006.01) | |
| A61B 90/00 | (2016.01) | |

(52) U.S. Cl.
CPC .......... *A61B 17/072* (2013.01); *A61B 17/115* (2013.01); *A61B 2017/00128* (2013.01); *A61B 2017/00367* (2013.01); *A61B 2017/00535* (2013.01); *A61B 2017/00539* (2013.01); *A61B 2017/00818* (2013.01); *A61B 2017/00827* (2013.01); *A61B 2017/07214* (2013.01); *A61B 2017/07257* (2013.01); *A61B 2017/306* (2013.01); *A61B 2090/065* (2016.02)

(58) Field of Classification Search
CPC ........... A61B 2017/07214; A61B 2017/00539; A61B 2017/00818; A61B 2017/07285; A61B 2017/00535; A61B 2017/00827
USPC .............. 227/19, 175.1, 175.2, 176.1, 180.1; 606/139, 153, 219
See application file for complete search history.

(56) References Cited

U.S. PATENT DOCUMENTS

| | | | |
|---|---|---|---|
| 5,906,625 | A | 5/1999 | Bito et al. |
| 6,197,022 | B1 | 3/2001 | Baker |
| 6,981,941 | B2 | 1/2006 | Whitman et al. |
| 7,225,964 | B2 * | 6/2007 | Mastri ................ A61B 17/0684 227/176.1 |
| 7,246,734 | B2 | 7/2007 | Shelton, IV |
| 7,380,696 | B2 * | 6/2008 | Shelton, IV ....... A61B 17/0686 227/175.1 |
| 7,559,452 | B2 | 7/2009 | Wales et al. |
| 7,708,181 | B2 | 5/2010 | Cole et al. |
| 7,832,408 | B2 * | 11/2010 | Shelton, IV ......... A61B 17/072 128/898 |
| 7,845,537 | B2 | 12/2010 | Shelton, IV et al. |
| 8,020,741 | B2 | 9/2011 | Cole et al. |
| 8,499,993 | B2 * | 8/2013 | Shelton, IV ....... A61B 17/0644 227/176.1 |
| 9,579,100 | B2 * | 2/2017 | Castro ................. A61B 17/068 |
| 2004/0094597 | A1 | 5/2004 | Whitman et al. |
| 2007/0102474 | A1 | 5/2007 | Shelton, IV et al. |
| 2007/0125826 | A1 | 6/2007 | Shelton, IV |
| 2008/0190989 | A1 | 8/2008 | Crews et al. |
| 2009/0236400 | A1 | 9/2009 | Cole et al. |
| 2011/0062212 | A1 | 3/2011 | Shelton, IV et al. |
| 2011/0295242 | A1 | 12/2011 | Spivey et al. |
| 2012/0181322 | A1 | 7/2012 | Whitman |

FOREIGN PATENT DOCUMENTS

| | | |
|---|---|---|
| WO | WO 02/17799 A1 | 3/2002 |
| WO | WO 2010/090941 A1 | 8/2010 |

OTHER PUBLICATIONS

Written Opinion of the International Searching Authority issued in International Appln. No. PCT/US2014/023123, filed on Mar. 11, 2014.

* cited by examiner

SYSTEM FOR CONTROLLING A TISSUE-STAPLING OPERATION

CROSS-REFERENCE TO RELATED APPLICATIONS

This application is a continuation of U.S. application Ser. No. 14/203,951, filed Mar. 11, 2014, which claims the benefit of priority from U.S. Provisional Application No. 61/801,344, filed Mar. 15, 2013. The entirety of each of the above-referenced applications is incorporated herein by reference.

FIELD OF THE INVENTION

The present invention relates to a system and method for controlling the operation of a tissue-stapling device, such as controlling the operation of a remote, intra-oral stapling device by controlling the amount and pressure of fluid to the device.

BACKGROUND

Tissue plication devices for capturing and stapling a tissue fold by remote access, e.g., for forming stapled tissue folds within the cavity of the stomach by means of intraoral access, are known. One such intraoral device, which functions to draw a tissue fold into an expandable tissue vacuum chamber, and staple the fold with an annular array of staples, is described in U.S. Pat. Nos. 8,020,741, 7,922,062, 7,913,892, 7,909,223, 7,909,222, 7909,219,7,721,932 and 7,708,181, all of which are incorporated herein by reference.

It would be desirable, in the operation of a tissue-plication device of the type described above, to be able to control tissue acquisition, compression, and stapling under conditions that optimize operation of the device, produce a stapled plication under reproducible conditions, and also allow for automatic operation or user intervention to initiate, pause and/or abort certain functions.

SUMMARY OF THE INVENTION

In one aspect, an endoscopic stapler is disclosed. The stapler may include a staple member and a staple holder. The staple holder may include one or more staples. The stapler holder may also include an anvil member spaced apart from the staple member, wherein the staple member and the anvil member are configured to relatively move towards one another. The staple holder may also include a controller fluidly coupled to the staple member through a plurality of conduits. The controller may be configured to (a) direct a pressurized fluid to the staple member through a first conduit of the plurality of conduits to relatively move the staple member and the anvil member towards one another, and (b) direct the pressurize fluid through a second conduit of the plurality of conduits to eject one or more staples from the staple holder.

Additionally or alternatively, in some aspects, the staple member may include a hydraulic chamber fluidly coupled to the controller through the plurality of conduits, the hydraulic chamber may include a first piston and a second piston therein, wherein the first piston may be configured to relatively move the staple member and the anvil member towards one another, and the second piston may be configured to eject one or more staples from the staple holder; the second piston may be positioned within the first piston; directing pressurized fluid through the first conduit may jointly move the first piston and the second piston from a first position to a second position, and directing pressurized fluid through the second conduit may move the second piston relative to the first piston from the second position to a third position away from the first position; the first conduit may be coupled to a first fluid source containing a predetermined quantity of fluid and the second conduit may be coupled to a second fluid source containing a predetermined quantity of fluid; the stapler may further include a first switch, the activation of which initiates the supply of pressurized fluid from the first fluid source through the first conduit; the stapler may further include a first sensor adapted to detect a pressure applied to the staple member in response to pressurized fluid in the first conduit; the stapler may further include a second switch, the activation of which initiates the supply of pressurized fluid through the second conduit; the second switch may be automatically activated when the first sensor indicates that a preselected pressure has been reached; and relative movement of the staple member and the anvil member towards one another may include (i) the staple member moving towards the anvil member, and (ii) the anvil member moving towards the staple member.

In another aspect, an endoscopic stapler is disclosed. The stapler may include a staple member including a hydraulic chamber with a first piston and a second piston positioned therein, and a staple holder including one or more staples positioned therein. The stapler may also include an anvil member spaced apart from the staple member. The staple member and the anvil member may be configured to relatively move towards one another. The stapler may further include a controller fluidly coupled to the hydraulic chamber. The controller may be configured to (a) jointly move the first piston and the second piston from a first position to a second position to relatively move the staple member and the anvil member towards one another, and (b) move the second piston relative to the first piston from the second position to a third position to eject one or more staples from the staple holder.

Alternatively or additionally, the controller may be fluidly coupled to the hydraulic chamber through a first conduit and a second conduit, wherein directing pressurized fluid through the first conduit may be effective to jointly move the first piston and the second piston from the first position to the second position, and directing pressurized fluid through the second conduit may be effective to move the second piston from the second position to the third position; the stapler may further include a first switch, the activation of which may initiate the supply of pressurized fluid through the first conduit, a first sensor configured to detect a pressure applied to the staple member in response to pressurized fluid in the first conduit, and a second switch, the activation of which initiates the supply of pressurized fluid through the second conduit, wherein the second switch may be automatically activated when the first sensor indicates that a preselected pressure has been reached; the controller may be coupled to a first fluid source and a second fluid source, wherein the controller may be configured to (i) direct fluid from the first fluid source to the hydraulic chamber to jointly move the first piston and the second piston from the first position to the second position, and (ii) direct fluid from the second fluid source to the hydraulic chamber to move the second piston from the second position to the third position; and relative movement of the staple member and the anvil member towards one another may include (i) the staple member moving towards the anvil member, and (ii) the anvil member moving towards the staple member.

In another aspect, a method of operating an endoscopic stapler including a staple member with one or more staples and an anvil member is disclosed. The method may include positioning the stapler within a patient, actuating a controller a first time, and actuating the controller a second time. Actuating the controller a first time may direct a pressurized fluid to the staple member through a first conduit to relatively move the staple member and the anvil member towards one another, and actuating the controller the second time may direct a pressurized fluid to the staple member through a second conduit to eject one or more staples from the staple member.

Alternatively or additionally, relatively moving the staple member and the anvil member towards one another may include (i) moving the staple member towards the anvil member, and (ii) moving the anvil member towards the staple member; the staple member may include a hydraulic chamber with a first piston and a second piston positioned therein, and actuating the controller a first time may include jointly moving the first piston and the second piston from a first position to a second position to relatively move the staple member and the anvil member towards one another; and actuating the controller a second time may include moving the second piston relative to the first piston from the second position to a third position to eject one or more staples from the staple member; the method may further include positioning tissue between the staple member and the anvil member before the step of actuating the controller a second time.

The invention includes, in one embodiment, an external controller for use in controlling the operation of a surgical staple device that includes (i) a stapler having staple and anvil members movable toward and away from one another to a capture position, for capturing at least one tissue layer therebetween, and first and second pistons controlling the movement of the staple and anvil members toward one another, and for ejecting one or more staples from the staple member, respectively, and (ii) a shaft having first and second fluid-carrying conduits connectable to the controller for communicating the controller with the first and second pistons in the device, respectively. The controller includes:
a. first and second fluid sources adapted to supplying pressurized fluid from the first and second fluid-carrying conduits in the shaft to the first and second pistons, respectively;
b. a first switch whose activation initiates the supply of pressurized fluid from the first fluid source to the first piston, to move the staple and anvil members toward one another;
c. a first sensor for sensing the pressure applied to the staple member at the capture position, in response to fluid supplied to the first piston; and
d. a second switch whose activation requires the sensing of a preselected pressure applied to the staple member at the capture position, and which initiates the supply of pressurized fluid from the second fluid source to the second piston, to drive a staple from the staple member through tissue captured between the staple and anvil members.

In various aspects, the first and second fluid sources may be liquid-carrying syringes; the second switch may be automatically activated to initiate supply of pressurized fluid from the second fluid source to the second piston after the sensor indicates that such preselected pressure has been reached; where the first fluid source is a liquid-carrying syringe, the first sensor measures the liquid pressure applied by the first source; for use in controlling the operation of a surgical stapling device in which the staple and anvil members are movable toward and away from one another along an axis, for acquiring a tissue fold within an expandable vacuum tissue-acquisition chamber defined between the staple and anvil members, the first and second fluid sources are liquid-carrying syringes and the controller include a second sensor for indicating the volume of fluid supplied from the first source to the first piston, as an indicator of the relative positions of the staple and anvil members, as they are moved toward one another. The controller may include a stepper motor that drives fluid from the first syringe by motor rotation, and the second sensor may function to determine the total rotation of the motor, as a measure of the volume of fluid supplied by the first fluid source. The first sensor may measure the liquid pressure produced by the first source.

In another aspect, the invention includes an external controller for use in controlling the operation of a surgical-staple device that includes a staple having staple and anvil members movable toward and away from one, from an open position to a tissue-acquisition position and from the tissue-acquisition position to a capture position, and first and second pistons controlling the movement of the staple and anvil members toward one another, and for ejection one or more staples from the staple member, respectively, and a shaft having first and second fluid-carrying conduits connectable to the controller for communicating the controller with the first and second pistons in the device, respectively. The controller comprises:
a. first and second liquid-carrying syringes adapted to supply pressurized liquid from the first and second syringes conduits in the shaft to the first and second pistons, respectively,
b. a first switch whose activation initiates the supply of pressurized liquid from the first syringe to the first piston, to move the staple and anvil members from their open to tissue-acquisition position,
c. a first sensor for sensing when the staple and anvil members are at their tissue-acquisition position, based on the volume of liquid supplied to the first piston, at which tissue is acquired between the two members,
d. a second switch whose activation initiates the supply of pressurized liquid from the first syringe to the first piston, to move the staple and anvil members from their tissue-acquisition position to their capture position,
e. a second sensor for sensing the pressure applied to the staple member at the capture position, in response to fluid supplied to the first piston, and
f. a third switch whose activation requires the sensing of a preselected pressure applied to the staple member at the capture position, and which initiates the supply of pressurized fluid from the second fluid source to the second piston, to drive a staple from the staple member through tissue captured between the staple and anvil members.

The controller may include a stepper motor that drives fluid from the first syringe by motor rotation, and the first sensor may function to determine the total rotation of the motor, as a measure of the volume of fluid supplied by the first fluid source. The controller may function to automatically acquire a tissue fold between the staple and anvil members when the members are in their tissue-acquisition position. For use with a stapler device that includes a vacuum tissue-acquisition chamber defined between the staple and anvil members, the controller may further includes a fourth switch for initiating the supply of vacuum to the chamber, to acquire a tissue fold therein. The fourth switch may be automatically activated to initiate supply of pressurized fluid from the second fluid source to the second piston after the first sensor indicates that the staple and anvil members are in their tissue-acquisition position.

In still another aspect, the invention includes a system for capturing and stapling one or more layers of tissue. The system includes a stapler device having staple and anvil members that can be moved together, to capture and staple one or more tissue layers between the two members, a liquid-carrying syringe for supplying pressurized liquid to a first piston in the device, whose activation causes the staple and anvil members in the device to move to a tissue-capture position at which the one or more tissue layers are captured between the staple and anvil members, a fluid line connecting the syringe to the first piston, a fluid release mechanism on the device between the line and piston, to allow air in the syringe and line to be removed before operation of the system, a sensor for sensing the pressure applied to the syringe, and a switch which prevents activation of the syringe during operation until a preselected pressure is sensed by the sensor. The fluid release mechanism may be, for example, a bleed screw.

These and other objects and features of the invention will become more fully apparent when the following detailed description of the invention is read in conjunction with the accompanying drawings.

DETAILED DESCRIPTION OF THE INVENTION

The present application describes a system and controller for controlling the operation of tissue-stapling device, such as a device for forming tissue plications within the stomach of a patient by intra-oral access. As will be detailed below, the tissue-stapling device includes a tissue-acquisition and stapling head and a shaft to which the head is attached at the shaft's distal end. The system of the invention includes the combination of controller and device, where the controller controls is connected to the proximal end of the shaft, and controls the various operations of the device as will be seen.

Figure 1A:
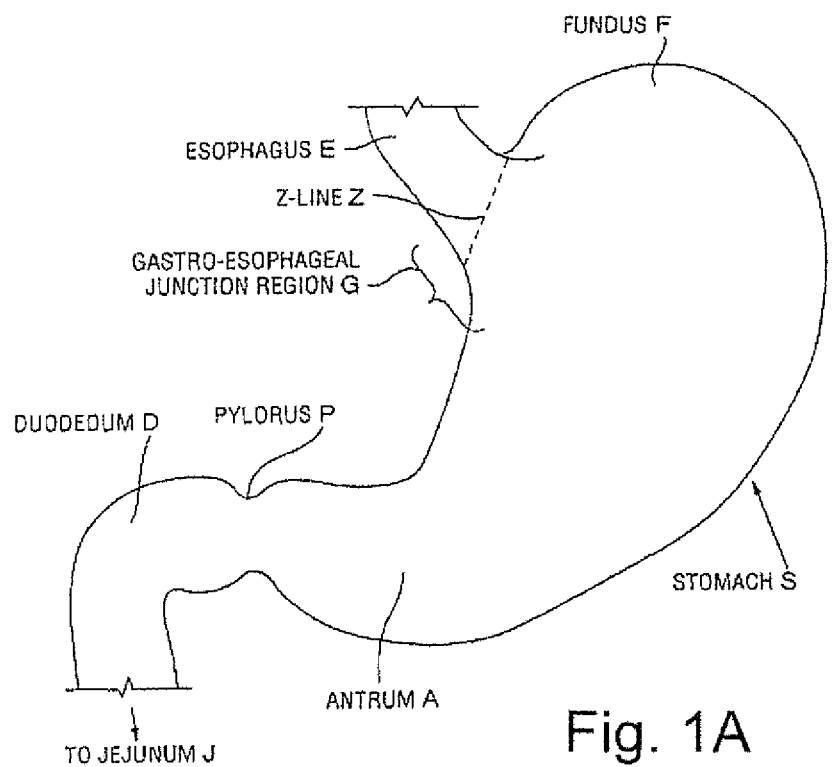
FIG. 1A is a schematic illustration of a human stomach and a portion of the small intestine, as known in the prior art.

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S. Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

A. Stapler System

Figure 1B:
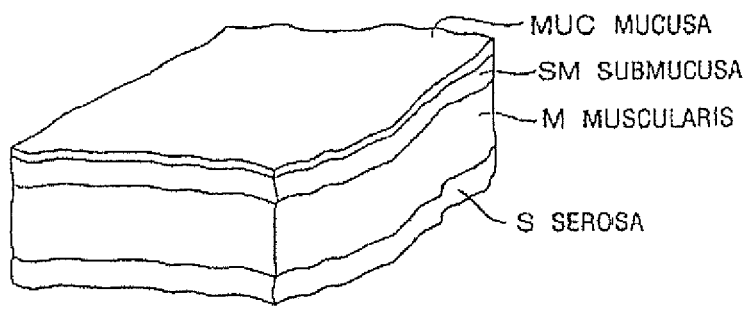
FIG. 1B is a cross-sectional perspective view of a portion of a stomach wall, illustrating the layers of tissue forming the wall, also as known in the prior art.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

In the disclosed invention, a stapler device having a stapler carried at the distal end of a shaft is introduced into the stomach intra-orally, via the esophagus. Typically the device is equipped with an endoscope that allows the physician to view the interior region of the stomach, and guiding structure by which the device can be positioned at a desired target location within the stomach, i.e., the region at which the device will form a tissue fold. When the stapler is placed against a tissue region, and vacuum is applied, a portion of the interior stomach wall is drawn inwardly into the device, forming a two-layer fold or plication that brings sections of serosal tissue on the exterior of the stomach into contact with one another. After bringing opposed sections of tissue together in a compressed state, the stapler is activated to deliver one or more fasteners, e.g., one or more staples, that will hold the tissue layers together until at least such time as serosal bonds form between them. Each of these steps may be performed wholly from the inside of the stomach and thus can eliminate the need for any surgical or laparoscopic intervention. After one or more plications is formed, medical devices (including, but not limited to any of the types listed above) may be coupled to the plication(s) for retention within the stomach.

The stapler device may include, in addition to a fastener for fastening tissue folds formed in the device, a blade that forms a hole or cut in a plication using the fastener-applying device. This hole or cut might be formed so that a portion of a medical implant may be passed through or linked to the hole/cut, or it may be formed so as to provoke a healing response that will contribute to the strength of the resulting tissue bond.

Figure 2:
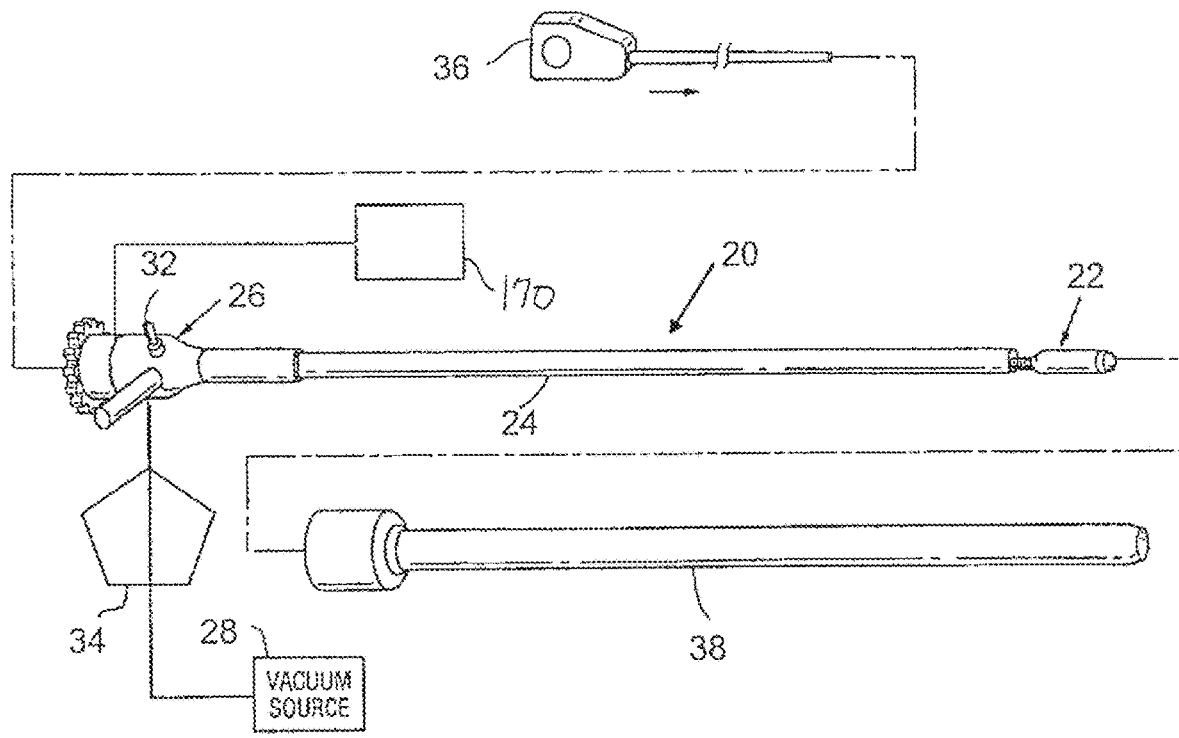
FIG. 2 illustrates a tissue-plication device constructed in accordance with an embodiment of the invention, also showing tools for intra-orally placing the device in a patient's s stomach.
Figure 3:
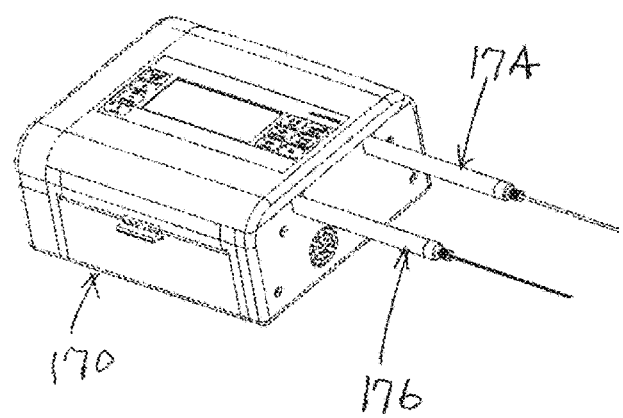
FIG. 3 is a perspective view of a tissue-plication device controller constructed according to an embodiment of the invention.

FIG. 2 illustrates one embodiment of a stapler device 20 which includes a stapler 22, for stapling one or more tissue layers, for example, for capturing and stapling a two-layer tissue fold or plication, and a flexible shaft 24 which carries the stapler at its distal end. The device is connected, at a distal-end handle portion 26 of the shaft, to a vacuum source 28 and to a controller 170, shown in perspective view in FIG. 3, for controlling various tissue acquisition, tissue compression, and tissue stapling operations in a manner to be described. As shown in FIG. 3, and described in detail below, the controller includes a pair of fluid-source assemblies, indicated at 174, 176 in FIG. 3, for supplying pressurized fluid, e.g., water, to first and second pistons in the stapler, through a pair of high-pressure lines (not seen) carried in the shaft. The controller fluid lines are connected to the shaft through fluid connections at the shaft handle portion, such as indicated at 32.

The vacuum source may be the "house vacuum" or vacuum pump. Also shown is an reservoir tank 34 connecting the vacuum source to the handle, for controlling the rate at which vacuum is applied to the tissue-acquisition device. Although not shown here, the vacuum source is connected to controller 30, which includes a switch (not shown) for connecting the vacuum source, e.g., pump, to the stapler, through a separate fluid line extending through the shaft.

An endoscope 36 in the system is insertable through a lumen in the shaft, and permits visualization of the plication procedure. The system may optionally include an overtube, such an endoscopic guide tube 38, having a lumen for receiving the shaft and attached device 22.

B. Exemplary Stapler

An exemplary stapler 22 for use with the controller of the invention is designed for acquiring a two-layer tissue fold, capturing the fold between staple and anvil members, and stapling the fold to form a tissue plication. It will be appreciated from below, however, that the controller of the invention can be used to control a variety of tissue staplers, including those designed for repair a single tissue layer, and those in which the staple and anvil members pivot toward one another, in a clamp-type motion, rather than move reciprocally toward and away from one another along an axis, as does stapler 22.

For purposes of description in this section, stapler 22 will be described with respect to its mechanical elements and to the operation of those elements illustrated in FIGS. 4A-4C and FIG. 5. It will be understood from below that the stapler illustrated in these figures also includes a flexible elastomeric sleeve (not shown) that covers the mechanical elements of the device, and which forms a vacuum chamber for tissue-acquisition between the staple and anvil members.

Figure 4A:
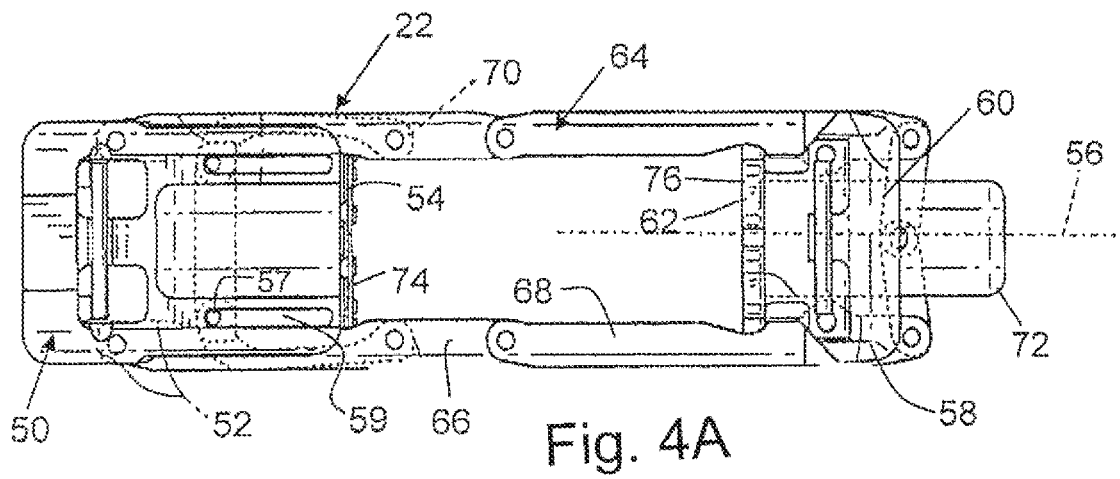
FIGS. 4A-4C are top plan views of the tissue-capture and stapling head in the plication device, showing the head in its low-profile condition (4A), during travel of the staple and anvil members toward a tissue-acquisition condition (4B), and the head in its tissue-capture condition (4C)
Figure 4B:
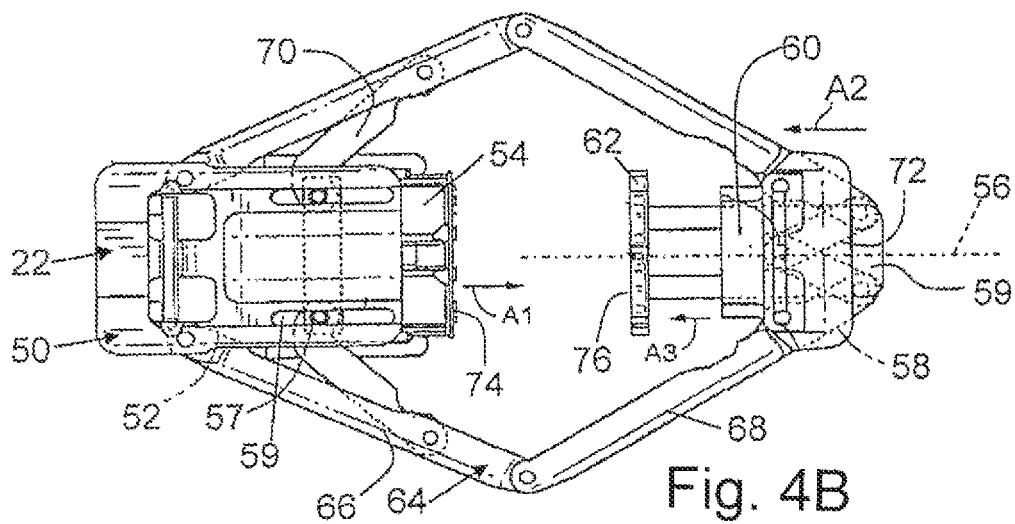
Figure 4C:
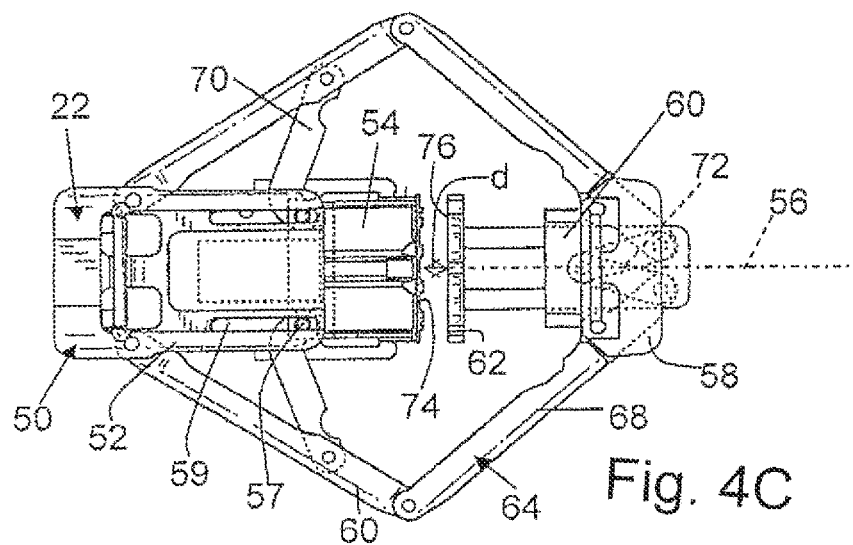

Stapler 22 is designed to have a minimum profile, shown in FIG. 4A, during insertion to the plication site; and is designed to expand to the progressively larger profiles seen in FIGS. 4B and 4C during a tissue-acquisition operation. Considering now the mechanical elements of stapler 22, a first or proximal or staple member 50 includes a housing 52 and a staple holder 54 that moves within the housing along an axis 56 extending in a horizontal direction in the figures. The extent of travel of the staple holder within the housing is limited by a pair of pins 57 that travel within slots 59 formed in the housing, as can be appreciated from the positions of the pins in FIGS. 4A and 4C. A second or distal or anvil member 58 includes a housing 60 and an anvil 62 that moves with its associated housing also along axis 56. The staple and anvil members are connected by a pair of arm assemblies 64 for movement toward and away from one another, along axis 56, between the low-profile condition shown in FIG. 4A and the fully expanded condition shown in FIG. 4C. Each arm assembly has proximal and distal arms 66, 68, respectively, that are pivotally joined to one another at their confronting ends, forming elbows in the assemblies, and are pivotally joined at their opposite ends to the associated member 50, 58, respectively.

A pair of spreader arms 70 are anchored within housing 52 through pins 57, and pivotally attached to associated assembly arms 66 at the opposite ends of the spreader arms. As can be appreciated from the figures, movement of staple holder 54 within its housing to the right in the figures, with corresponding travel of pins 57 within slots 59, acts to push spreader arms 70 outwardly, causing arms 66, 68 to spread outwardly and draw the two housings toward one another. At the same time, outward movement of arms 68 acts to move anvil 62 within its housing, toward the left in the figures, through a scissor-arm mechanism 72 connecting the distal ends of arms 68 to the anvil.

Figure 5:
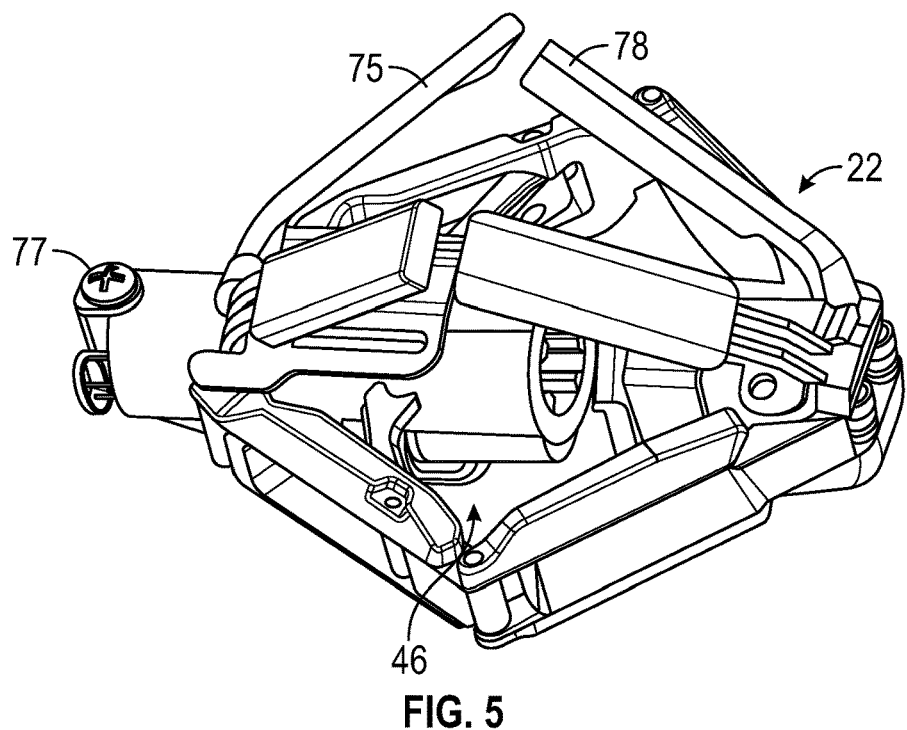
FIG. 5 is a perspective view of the head in the above plication device, showing a bleed screw for removing gas from the pressurized liquid lines supplying the pistons in the head.

Stapler 22 also has flexible lifter arms 78 whose opposite ends are pivotally joined to the proximal and distal members, as seen in FIG. 5. The lifter arm functions to expand the cross-sectional area of the chamber in conjunction with the expansion of the two arm assembles during operation of the device, as can be appreciated from FIG. 5. In an exemplary embodiment, a vacuum chamber 46 in the stapler, defined by the arm assemblies and spreader arm and the confronting faces of the staple and anvil members, has a cross-sectional area of about 0.7-.8 cm$^2$ in the low-profile condition shown in FIG. 4A, and a maximum cross-sectional area of 7-8 cm$^2$ in the fully expanded condition shown in FIG. 4C.

Also shown in FIG. 5 is a bleed screw 77 which allows pressurized fluid supplied to the stapler through the fluid conduits in the shaft to be drawn off, to ensure that the fluid pathway from controller 170 to the stapler is substantially free of air, as described below. The bleed screw is also referred to herein as a fluid-release mechanism between the fluid line and stapler pistons, to allow air or other gas in the syringe and line to be removed before operation of the system. Other release mechanism could include a spring-bias release button, for example.

Stapler movement is under hydraulic control, and includes a first piston for moving the staple and anvil relatively toward and away from another, from the open position or condition seen in FIG. 4C, to a tissue-acquisition position or condition at which tissue is drawn into tissue chamber 46 between the confronting faces of the staple and anvil members, such as shown in FIG. 4B, to a closed, capture position or condition, shown in FIG. 4C. The latter position is defined in exemplary stapler 22 by the farthest extent of travel allowed by the movement of pins 57 within slots 59, as described above, and places the staple and anvil members at a position with a gap d (FIG. 4C) between their confronting faces. That is, the stapler operates to capture a tissue fold and compress it to a total thickness d. Actual stapling, which occurs when a tissue fold is captured between the staple and anvil members at the capture position, is effected by a second piston that drives one or more staples out of the staple holder, through the captures tissue fold, and against the anvil, where the staple ends are bent against the "back" side of the fold, to form the tissue plication. As will be seen below, one object of the present invention is to control the operation of the two pistons in a way that the staple and anvil members are held in a sufficiently rigid configuration to produce a tight stapling of the tissue.

Figure 6A:
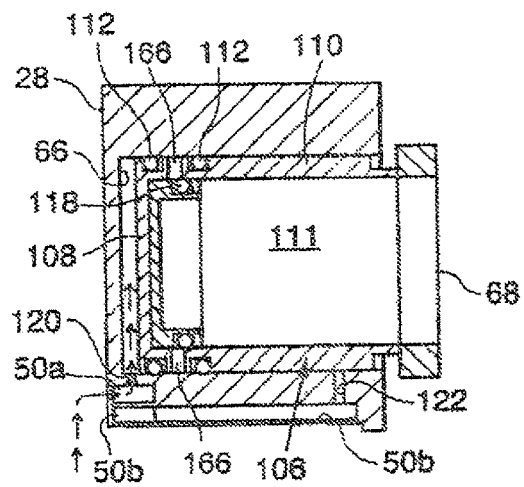
FIGS. 6A-6D are a series of schematic representations of the hydraulic chamber and pistons in an exemplary stapler used in conjunction with the controller of the invention.
Figure 6B:
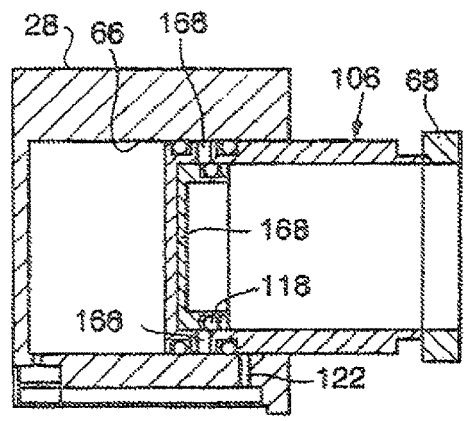

FIGS. 6A and 6B schematically show the fluid flow in the hydraulic chamber 66 of the staple housing 28 during both compression and stapling stages of actuation. Referring to FIG. 11A, compression piston 106 is disposed within hydraulic chamber 66. Disk 68 is positioned in contact with or slightly distal to piston 106. Compression piston 106 is generally cup-shaped, having a rear wall 108 and a side wall 110 enclosing an interior 111. O-ring seals 112 are spaced-apart on a proximal portion of the side wall 110. Channels 166 are formed through the side wall 110, between the o-ring seals 112.

A second piston, referred to as the staple piston 168, is positioned in the interior 111 of compression piston 106, against the rear wall 108. Although not shown in FIGS. 6A-6D, cutting element 86, with the staple pusher 76 thereon, is positioned in contact with or slightly distal to the staple piston 168. An o-ring seal 118 surrounds a portion of the staple piston 168 that is distal to the channels 166 in the compression piston.

Figure 6C:
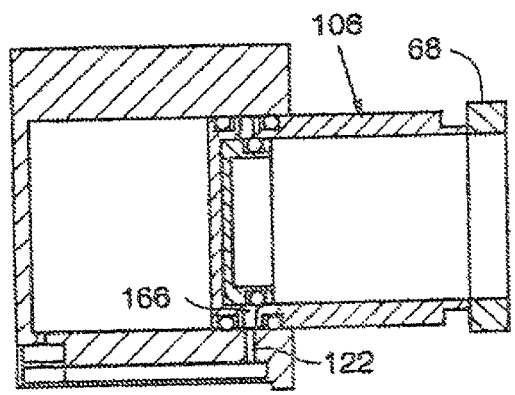
Figure 6D:
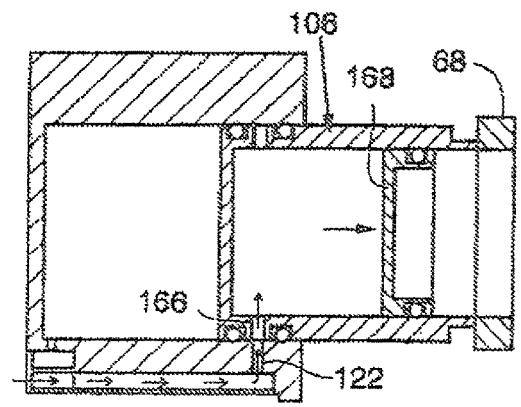

A first fluid channel 120 extends from fluid port 50a in the stapler housing 28 to a proximal section of the hydraulic chamber 66. A second fluid channel 122 extends from fluid port 50b in the stapler housing to a more distal section of the hydraulic chamber 66. Fluid flow from port 50a and fluid channel 120 against the compression piston cylinder is shown in FIG. 6A. Fluid pressure within the hydraulic chamber 66 advances the compression piston 106, with the stapler piston 168 within in it, in a distal direction. FIG. 6B shows the compression piston 106 approaching the end of its travel. Once the compression piston reaches the end of its travel as shown in FIG. 6C, channel 166 in the compression piston 106 aligns with channel 122 in the housing, allowing fluid introduced through fluid port 50b to enter the interior of the compression piston 106 via channel 122. The fluid entering the interior of the compression piston drives the staple piston distally as shown in FIG. 6D.

Actuation of the device is by compressed fluid supplied to a piston within housing 50 (not shown). This causes stapler 54 to move to the right in the figures relative to housing 50, as seen in FIGS. 4B and 4C, in turn causing the two spreader arms in the device to pivot away from one another, and forcing the two arm assemblies toward their expanded positions shown sequentially in FIGS. 4B and 4C. That is, actuation of the driving piston in the device causes the following sequence of events: (1) movement of the stapler within its housing along axis 56 toward the right in the figures, indicated by arrow A1 in FIG. 4B, (2) movement of the spreader arms and pivotally attached arm assemblies outwardly, away from axis 56, (3) movement of the two housings toward one another along axis 56, indicated by arrow A2 in FIG. 4B, (4) expansion of the spreader arm, and (5) movement of the anvil within its housing to the left along axis 56, indicated by arrow A3 in FIG. 4B. When the device has executed its full extent of travel, that is, when pins 57 reach their stop positions within slots 59, the stapler and anvil are positioned at a tissue-capture condition, seen in FIG. 4C, at which the confronting faces of the stapler and anvil, indicated at 74, 76, respectively, are separated by a gap d. In an exemplary embodiment, distanced is selected between 0.06-0.07 inches (e.g. for use with staples having legs of 5.5 mm length) or 0.105 to 0.115 inches for 6.5 mm leg length staples. Application of additional pressure into the hydraulic circuit will not compress the tissue any further.

A vacuum applied to the device at the same time or shortly after the mechanical elements are being driven toward their fully expanded condition, acts to draw tissue into the chamber. As it is being drawn in, the tissue fold expands outwardly, tending to fill the expanding cross section of the chamber, until the tissue chamber is fully expanded and the tissue fold is captured between the confronting faces of the stapler and anvil. Details of the device just described, and its mode or operation, are given in co-owned U.S. Pat. Nos. 8,020,741, 7,922,062, 7,913,892, 7,909,233, 7,909,222, and 7,909, 219, all of which are incorporated herein in their entirety. In particular, these patents describe in detail how staples are and ejected through a tissue.

With continued reference to FIGS. 4A-4C, stapler 22 includes a flexible-membrane covering not shown which covers the mechanical, tissue-capture elements of the device that are described below. The covering and certain mechanical elements that it covers form a vacuum chamber 46 in the device. The sleeve may be formed, for example, of silicone or other elastic, biocompatible material, and at least a central portion of the sleeve is sufficiently transparent to allow the user to view the interior of the tissue chamber during operation, to confirm (via endoscopic observation) that an appropriate volume of tissue has been acquired.

C. Controller

Figure 7:
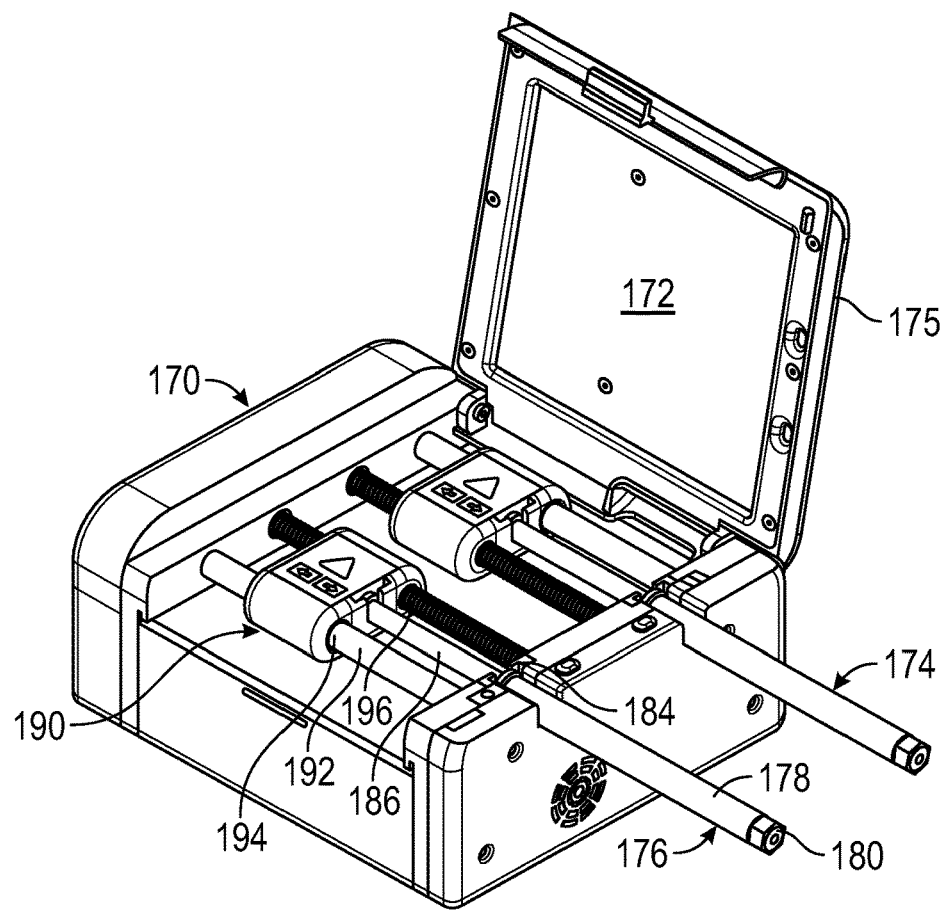
FIG. 7 is a perspective view of the controller in the invention, showing first and second syringes and pressures sensors in the controller.

FIG. 7 shows the controller 170 of the invention in perspective view. The controller is housed in a case 175 having an upper lid 172. Fluid-source assemblies 174, 176 in the controller supply fluid under pressure to the first and second pistons, respectively, in stapler 22, to control the operation of the stapler in accordance with the invention.

Fluid-source assembly 176, which is representative, includes a syringe 178 supported on case 175, and projecting outwardly therefrom. The syringe terminates at a distal fitting 180 connectable and to a socket, such as indicated at 32 on the handle portion of shaft 24 (FIG. 2), to form a fluid-tight connection with the stapler device. For mounting, the proximal flanged end of the syringe is snugly received in a U-shaped slot 184 formed in the side of case 175. A typical syringe is a stainless steel syringe having an 8 cc volume. Fluid, e.g., water, is expelled from the syringe under pressure by movement of a syringe plunger 186 in a left-to-right direction in the figure.

Figure 8:
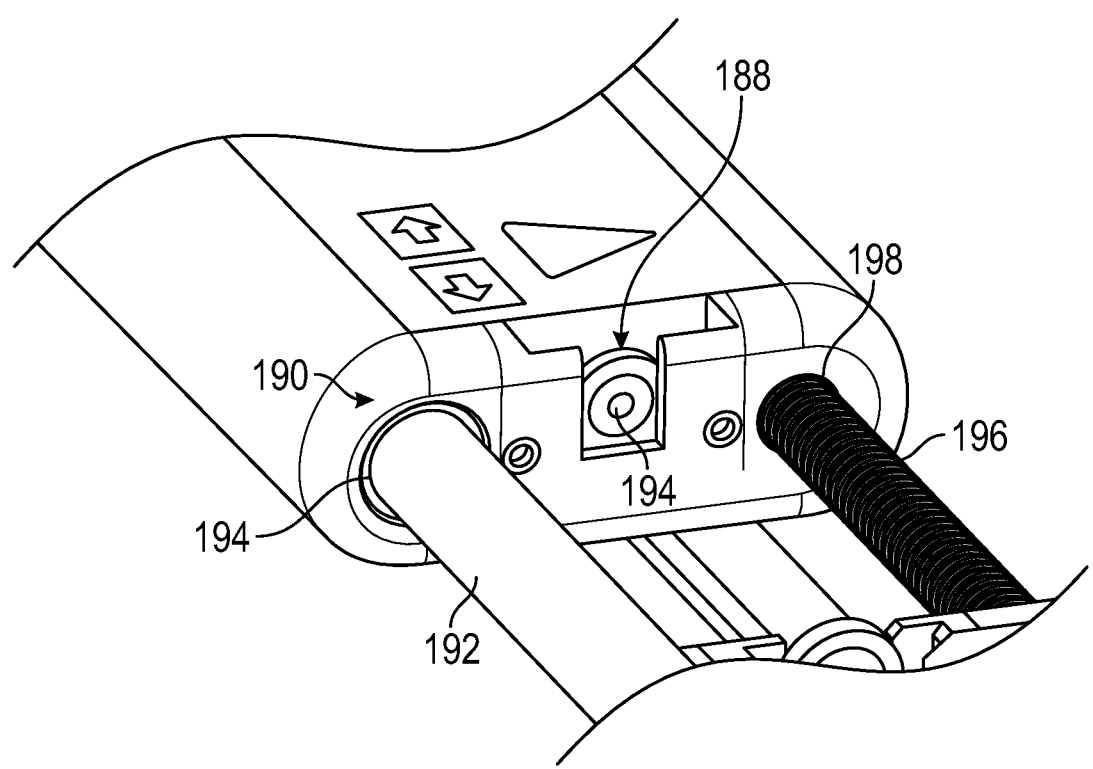
FIG. 8 is an enlarged view of a pusher unit in the controller.

With reference to FIGS. 7 and 8, plunger 186 is attached at its proximal flanged end in a U-shaped slot 188 formed on the side of a pusher unit 190, mounting the plunger for movement along the long axis of the syringe. A fixed mounting bar 192 is slid ably received in an opening 194 extending through the lower portion of the unit in the FIG. 7. A lead screw 196 is threadedly received in a threaded opening 198 extending through an upper portion of the unit in the figure.

Lead screw 196 is driven for rotational motion, in a direction that advances the pusher unit in a left-to-right direction in the FIG. 7 by a stepper motor (not shown) mounted in the controller to the left of the lead screw in FIG. 7. The stepper motor may be for example, a conventional 2-phase bipolar stepper motor with 1.8 degree step. When the stepper motor is activated, by one or more switches described below, the controller supplies a suitable current, e.g., 2.5 amps, to the motor through a clock circuit which records the time that the motor is on, i.e., activated. Rotation of the lead screw advances unit 190, forcing plunger 186 into the syringe and expelling syringe fluid, e.g., water, from the syringe into the stapler unit. The total volume of fluid expelled from the plunger can thus be measured by the total clock time for stepper-motor activation. The clock in the circuitry is also referred to herein as a sensor for sensing total volume expelled by the fluid source, i.e., syringe. Alternatively, syringe volume expelled could be monitored by any of a variety of optical, electrical, or magnetic position sensors capable of detecting the position of the plunger during plunger movement.

Figure 9:
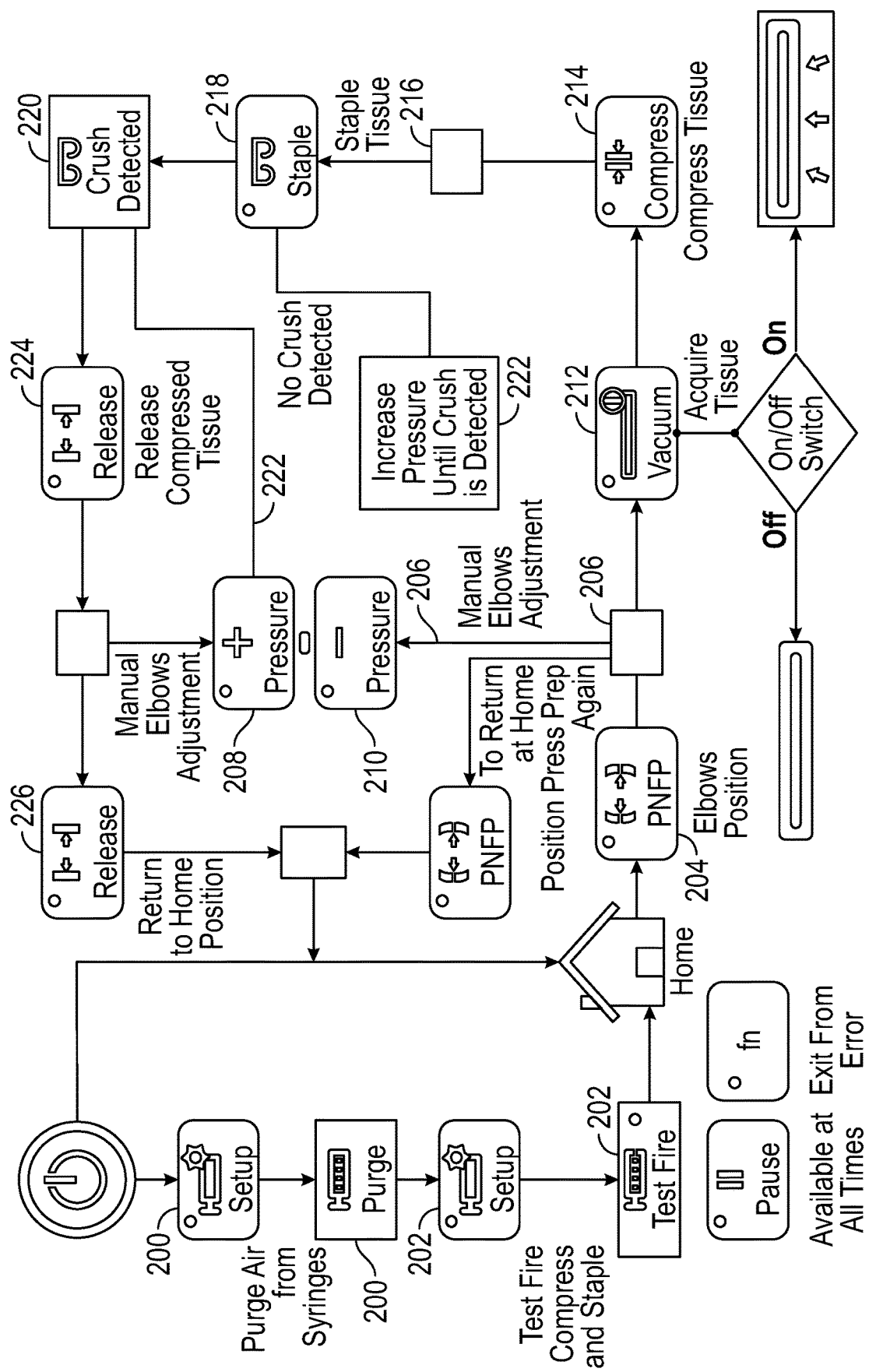
FIG. 9 is a diagram of operations carried out by the controller and user during operation of the controller in a tissue-stapling operation.

Unit 190 also includes a load-cell type pressure sensor 194 (FIG. 8) for sensing the force applied by unit 190 to the flanged end of plunger 186. The term "pressure sensor" is used interchangeably with "force sensor" herein since pressure and force are related by the syringe bore cross-sectional area. Sensor 194 is mounted on unit 190, within slot 188 for contacting the plunger flange received in the slot. The sensor may be, for example, a strain gauge or a capacitive sensor that measures movement of a diaphragm in response to increased physical pressure on the sensor. The range of sensor detection should preferably be in the 1,000-5000 psi range or higher. The sensor output, and the output from a force sensor associated with fluid-source assembly 174, are fed to a logic circuit in the controller whose components and operation will now be described with reference to FIGS. 9 and 10. The operation is described for the case where the hydraulic fluid supplied from the controller to the stapler is water or other suitable liquid. In the diagram in FIG. 9, the rounded rectangles are user buttons, the rectangles with heavy grey borders and enlarged font type are display buttons, and other boxes show controller operations. The buttons and display windows are displayed on the front of the controller panel.

To begin an operation, the user loads the syringes, mounts the loaded syringes in the controller, connects the syringe to the stapler device, and purges air from the system, e.g., by opening bleed screw 77 on the stapler, as described above and indicated at 200 in the figure. The vacuum source, e.g., pump, is also connected to the stapler device through the controller. When the "setup" button 200 on the controller is pressed, the controller sequentially activates the stepper motors of both fluid sources, forcing any air in a syringe or feeder line out of the system. In addition, the user may verify proper setup with a pressure check of both compression and stapling systems using the Test Fire functionality 202.

After guiding the stapler to a selected position within the patient's stomach, the user will initiate a tissue-acquisition step by pressing the "Prep" button 204. This will activate the first fluid source, supplying fluid to the first stapler piston to move the staple and anvil members in the stapler from their open position to their tissue-acquisition position, indicated as the "Elbows position" at 206 in FIG. 9. This position is achieved by supplying a selected volume of liquid, as measured by the syringe "on" time or motor step count, from the first fluid source to the first stapler piston. The controller will now either indicate at 206 that the stapler is ready for tissue acquisition, or invite the user to make a manual elbows adjustment by increasing or decreasing fluid pressure, as indicated by the adjustment loop 206 in FIG. 9. This loop allows the user to increase (208) or decrease (210) the amount of volume supplied to the first piston during the "elbow position" operation, for accurate placement of the stapler at its tissue-acquisition position.

When the desired tissue-acquisition position is reached, the controller can be set to either automatically activate the vacuum switch or wait for the user to press the vacuum button 212. In either event, a vacuum is applied to the stapler tissue chamber, drawing a tissue fold into the chamber. After tissue acquisition, the controller, either automatically or by user command by pressing "Compress" button 214, will then supply fluid to the first source to move the staple and anvil members to their compress position, where tissue is compressed in the fixed gap between the two staple members. Also after the staple and anvil members have moved to their compress position, the vacuum switch is closed, preventing unwanted suction on the tissue surrounding the fold. The force on the first syringe is now checked to ensure that a preselected pressure is being applied to the stapler, to hold the two stapler members at or above a preselected pressure that will ensure a successful stapling operation. This pressure, which is measured by the load cell in the first fluid source, is confirmed at display 216.

Once this pressure is confirmed, the controller, either automatically or by the user pressing the "Staple" button 218, will activate the second fluid source to initiate tissue stapling. The pressure measured by the second source is then used to determine if there has been a successful staple "crush" at 220. Here it will be appreciated that having a preselected pressure in the first fluid source ensures that the staple and anvil members will be held together with a force that is sufficient to resist the stapling force that acts to push the two members apart, ensuring the staple will be properly bent or "crushed" during a stapling operation. The crush event is reflected in the fluid pressure measured at the second source during a stapling operation and a "crush" is detected at 204. If a successful crush is not detected, the controller will proceed through a loop 222 that will allow the user to increase the second source pressure, to achieve crush. When a successful crush is obtained, the controller will release pressure to the second fluid source, by reversing the direction of the fluid-source stepper motor, to return the stapler to a ready position.

After second fluid source has released pressure, the controller can either automatically or on user command proceed to "release," at 224, and reduce the pressure supplied to the first fluid source, by reversing the direction of the fluid-source stepper motor, causing the staple and anvil members to move away from the compress position, and allow tissue release from the stapler. The controller will enable the user to manually control elbow adjustment by increasing or decreasing fluid pressure, as indicated by the adjustment options 208 and 210, which will enable the user to facilitate tissue release, Finally, the controller can either automatically, or on user command fully release pressure on the first syringe to "return to home position," at 226, which fully retracts the staple and anvil members.

To summarize operation the steps above, the user will:
Insert the stapler into the patient, after purging the system of gas, and position the stapler head at the desired location and set the tissue acquisition position with the PREP button.
Acquire tissue with the VACUUM button.
Compress tissue by pressing COMPRESS, after which vacuum turns off automatically at full compression pressure.
Press STAPLE to actuate the staple firing sequence.
Press RELEASE, to withdraw the stapler from the patient and perform the reloading procedure.

Figure 10:
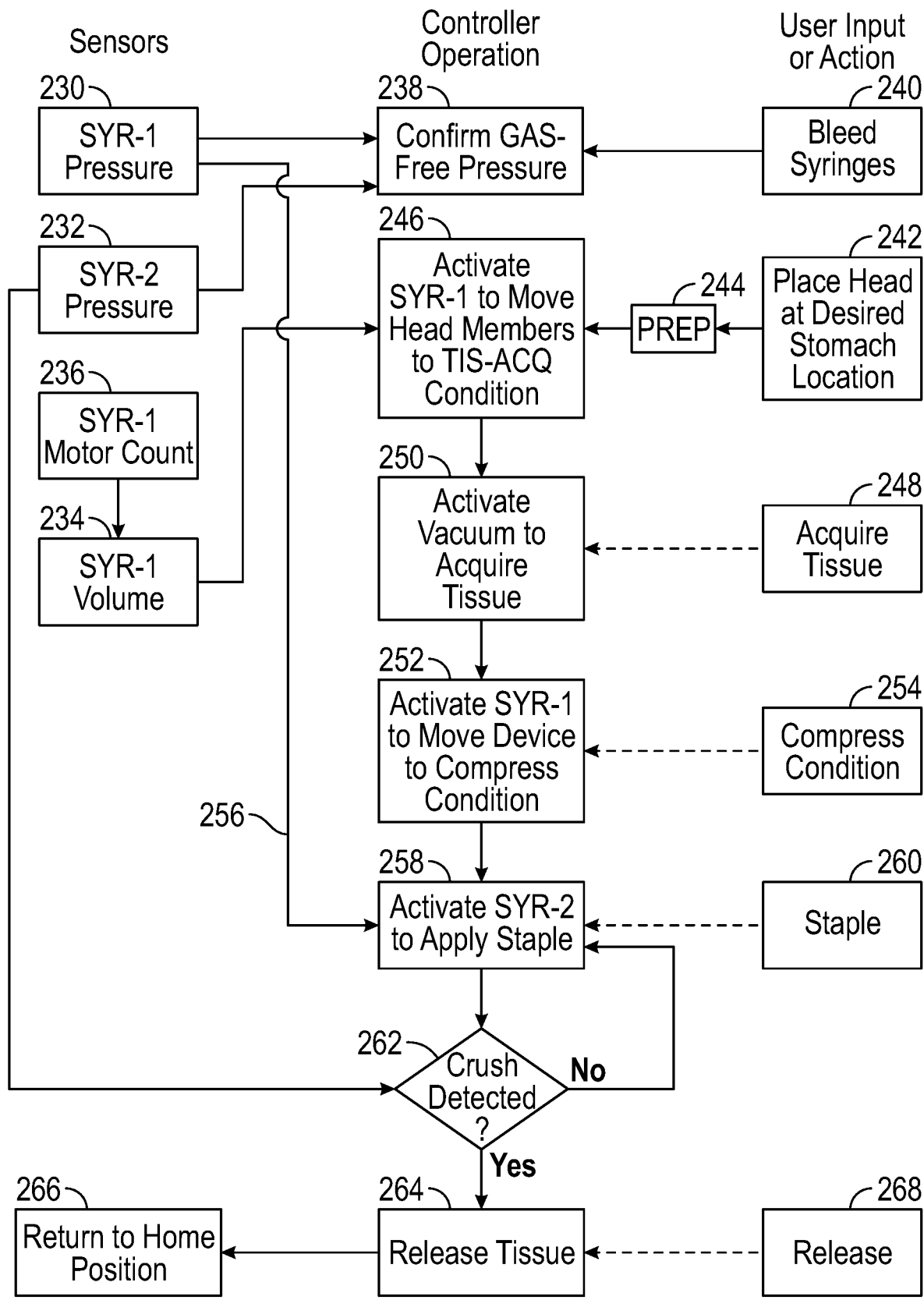
FIG. 10 is a flow diagram showing sensor and activation events associated with the logic circuit in the controller.

FIG. 10 describes the basic logic circuitry of the controller in terms of the sensor readings and user input during a stapling operation. As seen, the controller has three sensors that it responds to: first and second pressure (force) sensors 230, 232, respectively, and a volume sensor 234 based on stepper motor rotation count 236 in the first fluid source. The first controller operation, at 238, confirms that the fluid lines and syringe are gas-free, using pressure measurements from both fluid sources, after the fluid lines have been bled at 240 to release entrapped gas. Alternatively, the controller could confirm gas-free lines by activating the fluid sources for a time sufficient to purge any gas in the lines, before connecting the lines to the stapler as described.

After placing the stapler in the patient at a desired location, at 242, the user will press Prep at 244 to signal the controller activate Syringe-1 to move staple and anvil members to their tissue-acquisition condition 246. When the stapler reaches this condition, based on Syringe-1 volume determination from volume sensor 234, the controller will either switch on vacuum, for tissue acquisition (250), or signal the user that the staple is ready for tissue acquisition, by switching on vacuum (248).

After a suitable period for tissue acquisition, e.g., 2-5 seconds, the controller will either automatically activate the first fluid source to move the stapler members to their compress position (252) or signal that user that the system is now ready for the tissue compress stage, at 254. During the period when the staple and anvil members are moved from their tissue-acquisition to tissue-compress positions, the controller operates to switch off vacuum, causing a gradual loss in vacuum in the tissue chamber, as the tissue is being captured between the two staple members.

At this stage, the controller will check the pressure on Syringe-1 at 256 to confirm that the staple member is held at the compress condition with enough force to adequately resist the tendency of the staple and anvil members to move away from one another during stapling. With this force confirm, the controller will either automatically activate Syringe-2 for stapling, at 258, or signal the user that the system is ready for staple activation at 260.

During the stapling operation, the controller monitors pressure from Syringe-2 to determine if the pressure applied to the syringe is sufficient to produce a staple "crush," at 262. If insufficient pressure is detected, the controller will increase the pressure in both Syringe-1 and Syringe-2 until a sufficient crush pressure is achieved. If sufficient crush pressure is measured, the controller will either automatically operate the fluid sources to allow release of stapled tissue (264) and return to the stapler home position (266), or signal the user that it is safe to perform these functions, at 268.

In addition to these basic function, the controller has built into its circuitry a number of features that prevent unwanted actions, either by the user or the stapler, including the features that:

1. The Vacuum button must be held down to activate vacuum except when tissue acquisition is imminent (PREP position). This prevents the stapler from acquiring tissue inadvertently, especially while entering the stomach.
2. The vacuum switches off once compression pressure reaches a set value. This prevents injuring the stomach tissue through prolonged suction.
3. The vacuum cannot be switched on with a momentary press of button except during tissue acquisition. This prevents the vacuum from remaining on without user input except when tissue acquisition is imminent (PREP position).
4. The stapling pressure is always released before compression pressure. This prevents overload condition on certain mechanical connections within stapler head.
5. Pressure ramp is monitored and compared to expected values. This prevents use of system if setup, specifically de-airing of syringes, has not been performed properly.
6. Certain buttons are locked out in certain states. Inappropriate actions are prevented by deactivation of buttons.
7. Expanding stapler head can only occur with 3 second button activation. This prevents inadvertent stapler head expansion.
8. Tissue release is managed by staged collapse of stapler head back to insertion profile, and manual pressure control is active to facilitate tissue release. This reduces likelihood of tissue captured in stapler head mechanism during release of tissue.
9. User override of pressure is limited to 20% above that required for proper stapler function. This prevents user from overriding system to the point of stapler or Hydro-Force damage.
10. The position of the syringe plunger is monitored. This prevents actuation of stapler if fluid level is insufficient, or leak rate is outside of certain limits.
11. Pause is available at all times except when stapling is occurring.
12. Door and syringe interlocks prevent actuation if door is open or syringe is absent.

While the invention has been described with respect to certain embodiments, and operations, it will be appreciated that various modifications may be made without departing from the spirit of the invention.

What is claimed is:

1. A method of operating an endoscopic stapler including (a) a staple member with one or more staples and (b) an anvil member, comprising:
    positioning the stapler within a body;
    advancing a first pusher unit relative to a first fluid source of a controller operably coupled to the stapler to direct a pressurized fluid through a first conduit to relatively move the staple member and the anvil member towards one another, wherein the controller includes a sensor that measures an amount of pressurized fluid directed through the first conduit based on an amount of time a current supplied by the controller is activated; and
    advancing a second pusher unit of the controller relative to a second fluid source to direct a pressurized fluid through a second conduit to eject one or more staples from the staple member.

2. The method of claim 1, further comprising sensing a pressure applied to the staple member in response to the pressurized fluid in the first conduit.

3. The method of claim 2, further comprising, when a preselected pressure is sensed, automatically advancing the second pusher unit.

4. The method of claim 1, wherein relatively moving the staple member and the anvil member towards one another includes (i) moving the staple member towards the anvil member, and (ii) moving the anvil member towards the staple member.

5. The method of claim 1, wherein the staple member includes a hydraulic chamber with a first piston and a second piston positioned therein, and advancing the first pusher unit results in jointly moving the first piston and the second piston from a first position to a second position to relatively move the staple member and the anvil member towards one another.

6. The method of claim 5, wherein advancing the second pusher unit results in moving the second piston relative to the first piston from the second position to a third position to eject one or more staples from the staple member.

7. The method of claim 1, further including positioning tissue between the staple member and the anvil member before the step of advancing the second pusher unit.

8. The method of claim 1, wherein the first pusher unit is fixed to a first plunger, and advancing the first pusher unit moves the first plunger into the first fluid source.

9. The method of claim 8, wherein the second pusher unit is fixed to a second plunger, and advancing the second pusher unit moves the second plunger into the second fluid source.

10. The method of claim 1, wherein the first and second fluid sources each includes a longitudinal axis, and the longitudinal axes of the first and second fluid sources are parallel to each other.

11. A method of operating an endoscopic stapler including (a) a staple member with one or more staples and (b) an anvil member, comprising:

positioning the stapler within a body, the stapler being operably coupled to a controller that includes a first member in fluid communication with a first conduit and a second member in fluid communication with a second conduit, wherein each of the first conduit and the second conduit extends from the controller to a hydraulic chamber of the stapler;

advancing the first member into a first container to direct a fluid from the first container through the first conduit and into the hydraulic chamber to relatively move the staple member and the anvil member towards one another; and advancing the second member into a second container to direct a fluid from the second container through the second conduit and into the hydraulic chamber to eject one or more staples from the staple member.

12. The method of claim 11, wherein the first member is a first plunger, and the second member is a second plunger.

13. The method of claim 11, wherein the first and second members are parallel to each other.

14. A method of operating an endoscopic stapler including (a) a staple member with one or more staples and (b) an anvil member, comprising:

positioning the stapler within a body;

rotating a first member to direct fluid through a first conduit to relatively move the staple member and the anvil member towards one another; and rotating a second member to direct fluid through a second conduit to eject one or more staples from the staple member.

15. The method of claim 14, wherein the first member is a lead screw, and the second member is a lead screw.

16. The method of claim 15, wherein:

rotating the first lead screw advances a first pusher unit fixed to a first member, causing the first member to advance into a first fluid source to direct fluid through the first conduit; and rotating the second lead screw advances a second pusher unit fixed to a second member, causing the second member to advance into a second fluid source to direct fluid through the second conduit.

17. The method of claim 14, further comprising:

sensing a pressure applied to the staple member; and when a preselected pressure is reached, rotating the second member.

18. The method of claim 14, further comprising applying a vacuum to draw tissue between the staple member and the anvil member.

* * * * *